United States Patent [19]
Gruning et al.

[11] Patent Number: 5,470,992
[45] Date of Patent: * Nov. 28, 1995

[54] METHOD FOR THE SYNTHESIS OF BETAINES CONTAINING ≦10 PPM OF ORGANICALLY BOUND CHLORINE

[75] Inventors: Burghard Gruning; Willi Foitzik, Bottrop; Christian Weitemeyer; Hans-Dieter Kaseborn, both of Essen, all of Germany

[73] Assignee: Th. Goldschmidt AG, Essen, Germany

[*] Notice: The portion of the term of this patent subsequent to Oct. 11, 2011, has been disclaimed.

[21] Appl. No.: 212,540

[22] Filed: Mar. 14, 1994

Related U.S. Application Data

[63] Continuation of Ser. No. 15,489, Feb. 9, 1993, abandoned.

[30] Foreign Application Priority Data

Feb. 26, 1992 [DE] Germany ................ 42 05 880.5

[51] Int. Cl.⁶ .................................................. C07C 231/00
[52] U.S. Cl. ...................... 554/69; 554/52; 554/68; 554/103; 554/106
[58] Field of Search .................... 554/103, 52, 68, 554/106, 69

Primary Examiner—José G. Dees
Assistant Examiner—Deborah D. Carr
Attorney, Agent, or Firm—Anderson Kill Olick & Oshinsky

[57] ABSTRACT

A method for the synthesis of betaines of the general formula

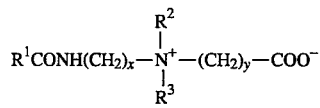

by quaternizing the fatty acid amide dialkylamines of the general formula

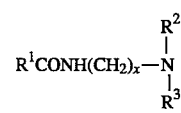

with ω-halogenalkylcarboxylic acids of the formula $X-(CH_2)_y COOH$, wherein X is a halogen group, or their salts in aqueous solution, the reaction being carried out within a temperature range of 115° to 180° C., until organically bound chlorine can no longer be detected, the fatty acid amide dialkylamine optionally being quaternized partially or completely in a first step at 80° to 100° C.

3 Claims, 1 Drawing Sheet

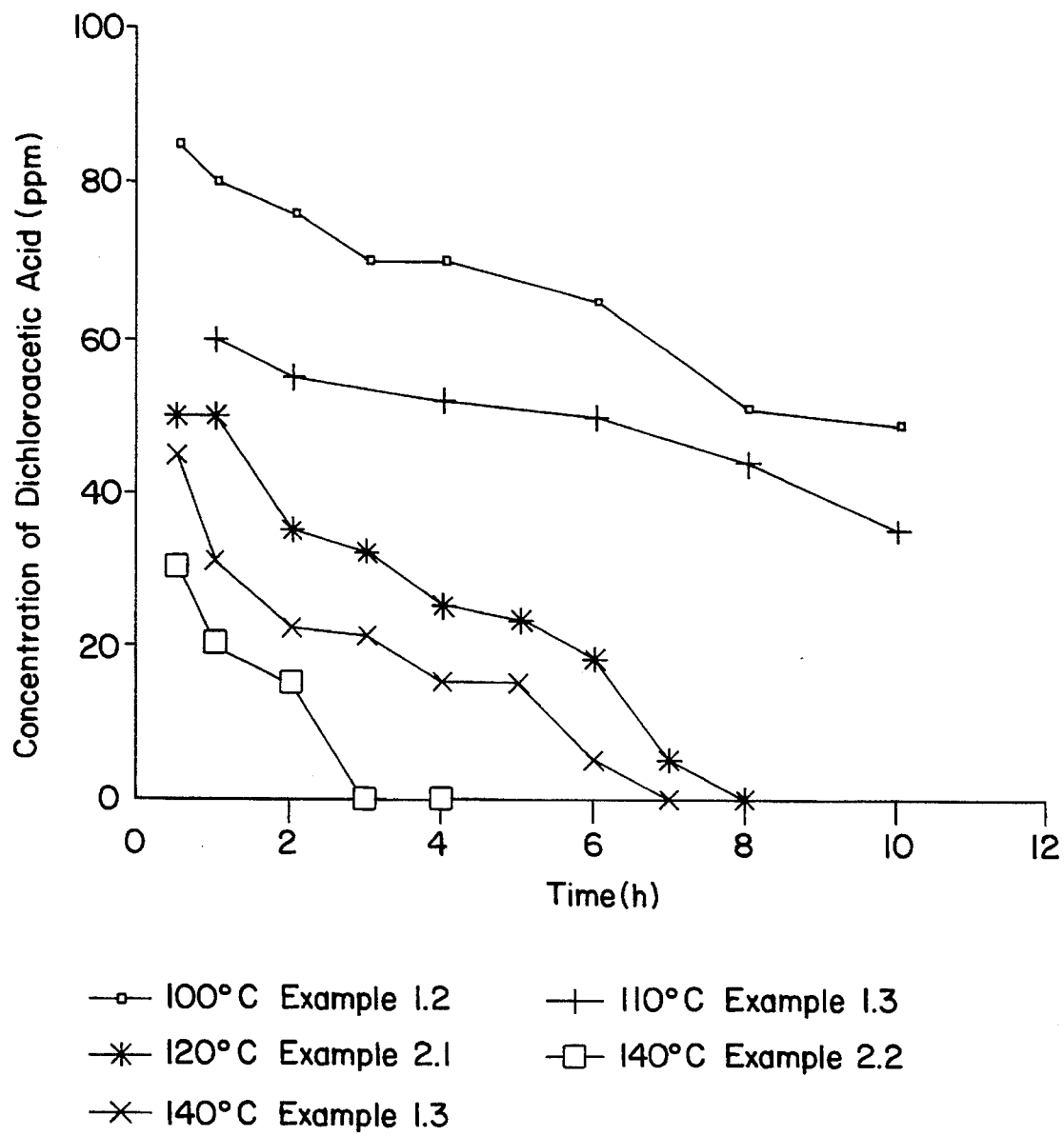

METHOD FOR THE SYNTHESIS OF BETAINES CONTAINING ≦10 PPM OF ORGANICALLY BOUND CHLORINE

This is a continuation application of Ser. No. 08/015,489, filed Feb. 9, 1993, now abandoned.

FIELD OF INVENTION

The invention relates to a method for the synthesis of betaines of the general formula

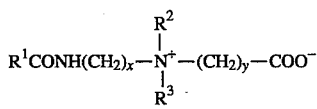

by quaternizing the fatty acid amide dialkylamines of the general formula

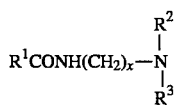

with ω-halogenalkylcarboxylic acids of the formula $X\text{-}(CH_2)_y COOH$, wherein X is a halogen group, or their salts in aqueous solution.

BACKGROUND INFORMATION AND PRIOR ART

Betaines are used on a large scale for the preparation of soaps and detergents for the body and particularly for the preparation of hair shampoos. Efforts are therefore made to prepare betaines which are free of impurities that can cause skin irritations or are otherwise undesirable for physiological reasons.

The German patent 29 26 479 discloses a method of the abovedescribed type, which is characterized in that the quaternizing reaction is carried out in an alkaline solution, which has a pH of 7.5 to 10.5 measured at 98° C.

By maintaining the pH within this range during the quaternization reaction, the fatty acid amide dialkylamine can no longer be detected by thin-layer chromatography after a reaction time of about three hours, the limit of detection being at about 0.02% by weight. If the reaction time is increased to about 8 to 10 hours, the content of organically bound chlorine in the reaction product is also decreased. However, by refining the analytical methods, it has been possible to show that residual amounts of compounds with organically bound chlorine, particularly sodium dichloroacetate, are still contained in the betaine obtained even under these conditions. The use of a pH higher than 10.5 also leads only to an inadequate decrease in the residual amounts of chloroacetic acids. Moreover, excessively long reaction times would be required for this, which are prohibitive for economic reasons. Furthermore, the danger exists of increasingly decomposing the starting materials or the betaines formed as a result of, for example, the hydrolysis of the amide bond. Above a pH of 10.5, the decomposition of the product can also be expected.

The German Offenlegungsschrift 39 39 264 relates to a method for lowering the residual content of free alkylating agent in aqueous solutions of amphoteric or zwitterionic surfactants, with the distinguishing feature that the solutions are given an aftertreatment with ammonia, an amino acid with 2 to 8 carbon atoms or an oligopeptide. The residual content of free alkylating agent, particularly of chloroacetic acid, is to be reduced to values of less than 0.01% by weight (based on the solids content) by this aftertreatment. It is, however, a serious disadvantage of this method that an additional step is required. A further disadvantage lies in that the reactions products of the alkylating agent with ammonia, an amino acid or an oligopeptide remain as impurities in the product.

OBJECT OF THE INVENTION

An object of the present invention is the synthesis of a betaine which is free of impurities, particularly free of compounds with organically linked chlorine, such as sodium monochloroacetate and dichloroacetate. Thus, a separate, additional step in the synthesis is avoided.

SUMMARY OF THE INVENTION

The invention relates to a method for the synthesis of betaines of the general formula

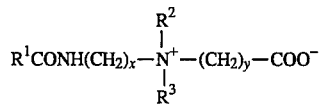

wherein
$R^1CO$ is an acyl group derived from a fatty acid or a fatty acid mixture with 6 to 8 carbon atoms,
$R^2$ and $R^3$ are the same or different and represent alkyl groups with 1 to 4 carbon atoms,
$x=2$ or $3$ and
$y=1$, 2 or 3,
by quaternizing the fatty acid amide dialkylamines of the general formula

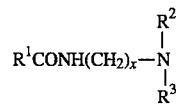

with ω-halogenalkylcarboxylic acids of the formula $X\text{-}(CH_2)_y COOH$, wherein X is a halogen group, or their salts in aqueous solution.

More particularly, the invention relates to a method, which enables betaines to be synthesized, which are free of organically linked chlorine and, in particular, free of sodium monochloroacetate and dichloroacetate.

As $R^1COOH$ carboxylic acids, particularly saturated and unsaturated fatty acids can be used, as well as mixtures of fatty acids, particularly of coconut fatty acids and palm kernel fatty acids.

This objective is surprisingly accomplished pursuant to the invention owing to the fact that the reaction is carried out within a temperature range from 115° to 180° C. until organically bound chlorine can no longer be detected, the fatty acid dialkylamine being optionally quaternized partially or completely in a first step at 80° to 100° C.

Preferably, the reaction is carried out at a temperature of 120° to 160° C., particularly at a temperature of 120° to 140° C. The reaction time, after which organically bound chlorine can no longer be detected, is about 1 to 10 hours depending on the temperature.

It may be advantageous to quaternize the fatty acid dialkylamine first partially or completely in a preliminary reaction at 80° to 100° C. and to carry out the decomposition of the organically bound chlorine subsequently at an elevated temperature of at least 115° C. Since the quaternization reaction and the decomposition reaction of the organically bound chlorine take place competitively at the elevated temperature, an amount of halogenated alkyl carboxylic acid in excess of the stoichiometric amount must be used for the one step method of the reaction. However, if the quaternization reaction is carried out partially or completely already in a first step at a temperature of 80° to 100° C., it is possible to carry out the reaction with stoichiometric amounts or with only a slight excess of halogenated alkyl carboxylic acid.

In view of the temperatures chosen, it is necessary to work in a closed system, such as an appropriately dimensioned stirred autoclave.

The lower limit of the temperature range of 115° C. is determined by the onset of the decomposition of sodium dichloroacetate. Below this temperature, the decomposition proceeds, if at all, only within a period, which is economically not acceptable for a commercial method. The upper limit of the temperature range of 180° C. is determined by the onset of the decomposition of the product or of the reactants.

With the inventive method, it is possible to lower the content of sodium monochloroacetate and dichloroacetate in the betaine solution below the respective limit of detection of less than 10 ppm.

The inventive method has the advantage that there is no need to add reagents, which contaminate the product, to decompose the organic chlorinated products.

Admittedly, in the German Offenlegungsschrift 27 23 120, the synthesis of a compound of the formula

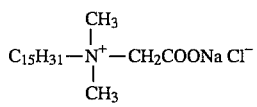

by the conversion of the corresponding dimethylalkylamine at 120° to 130° C. is described in one Example. Since the chlorine content of this product is stated to be 11.5%, this Example does not suggest transferring this procedure to betaines, which are derived from a fatty acid amide dialkylamine and for which, moreover, the risk of hydrolytically splitting the amide bond must be feared.

In the following Examples, the inventive method is described in even greater detail in comparison with the method of the state of the art, as given by the German patent 29 26 479. It should be understood that the Examples are given by way of illustration and not by way of limitation.

In the following Examples, coconut fatty acids aminoamide is used as fatty acid amide. It is synthesized by the amidation of coconut fatty acids with 3-N,N-dimethylaminopropylamine and has a tertiary nitrogen content of 4.6% by weight, as determined by titration. The titration is carried out with 0.1M hydrochloric acid, bromophenol blue being used as indicator. As sodium monochloroacetate, a product of conventional, commercial quality is used, which contains about 0.1% by weight of sodium dichloroacetate as impurity.

1. Synthesis of the Betaine, which corresponds to the German Patent 29 26 479 and is not of the Invention 1.1 Coconut fatty acids aminoamide (360 g) is added to a solution of 128 g (1.1 moles) of sodium monochloroacetate in 828 g of water, mixed with 5.3 g of 40% sodium hydroxide solution and heated in a 3-neck flask with stirrer to 98° C. Samples are taken at regular intervals and analyzed for their sodium monochloroacetate and sodium dichloroacetate contents by means of capillary electrophoresis.

After 8 hours of reaction time the sodium monochloroacetate content <10 ppm and the sodium dichloroacetate content is 35 ppm.

1.2 In a stirred autoclave, 360 g of coconut fatty acids aminoamide is added to a solution of 139.7 g (1.2 moles) of sodium monochloroacetate in 828 g of water and mixed with 5.3 g of 40% aqueous sodium hydroxide solution. The pressure is adjusted to 7 bar with nitrogen. Subsequently the temperature is raised to 100° C. Samples are taken at regular intervals and analyzed for their sodium monochloroacetate and sodium dichloroacetate contents. The reaction is stopped after 10 hours. The product is characterized by the following data:

| | |
|---|---|
| solids content: | 35% by weight |
| sodium chloride content: | 5.5% by weight |
| coconut fatty acids aminoamide content: | ca. 0.1% by weight |
| sodium monochloroacetate: | 115 ppm |
| sodium dichloroacetate: | 60 ppm |

Example 1.2 shows that the content of organically bound chlorine in the betaine cannot be reduced by increasing the pressure. The increased content of sodium monochloroacetate and sodium dichloroacetate is attributable to the fact that more sodium monochloroacetate and sodium dichloroacetate have been added than in Example 1.1.

1.3 The method of Example 1.2 is repeated. However, a reaction temperature of 110° C. is selected, at which a pressure of approximately 1.5 bar results. The reaction is stopped after 10 hours. The product is characterized by the following data:

| | |
|---|---|
| solids content: | 35% by weight |
| sodium chloride content: | 5.5% by weight |
| coconut fatty acids aminoamide content: | ca. 0.1% by weight |
| sodium monochloroacetate: | <10 ppm |
| sodium dichloroacetate: | 35 ppm |

Example 1.3 shows that, at a temperature of 110° C. and while maintaining the stoichiometry of the reaction formulation of Example 1.2, the sodium monochloroacetate content falls below 10 ppm. However, the sodium dichloroacetate content still amounts to 35 ppm.

2. Inventive Synthesis of the Betaine.

2.1. Coconut fatty acids aminoamide (360 g) is added to a solution of 139.7 g (1.2 moles) of sodium monochloroacetate in 828 g of water and heated in a stirred autoclave to 120° C., the pressure increasing to about 2 bar. Samples are taken at regular intervals. The reaction is stopped after 8 hours. The product is characterized by the following data:

| | |
|---|---|
| solids content: | 35% by weight |
| sodium chloride content: | 5.5% by weight |
| coconut fatty acids aminoamide content: | ca. 0.1% by weight |
| sodium monochloroacetate: | <10 ppm |
| sodium dichloroacetate: | <10 ppm |

2.2 The same reaction formulation as in Example 2.1 is heated in the stirred autoclave to 140° C., the pressure increasing to about 3.5 bar. The reaction is stopped after 4 hours. The product is characterized by the following data:

| | |
|---|---|
| solids content: | 35% by weight |
| sodium chloride content: | 5.5% by weight |
| coconut fatty acids aminoamide content: | ca. 0.1% by weight |
| sodium monochloroacetate: | 10 ppm |
| sodium dichloroacetate: | <10 ppm |

2.3. The method of Example 2.2 is repeated. However, no sodium hydroxide solution is added. The reaction is stopped after 8 hours. The product is characterized by the following data:

| | |
|---|---|
| solids content: | 35% by weight |
| sodium chloride content: | 5.5% by weight |
| coconut fatty acids aminoamide content: | ca. 0.1% by weight |
| sodium monochloroacetate: | <10 ppm |
| sodium dichloroacetate: | <10 ppm |

2.4. The method of Example 2.2 is repeated. However, the reaction mixture is heated in the stirred autoclave to a temperature of 160° C., the pressure increasing to about 4.5 bar. After only 1 hour of reaction time, the sodium dichloroacetate content is determined to be less than 10 ppm. The reaction is stopped after 4 hours. The product is characterized by the following data:

| | |
|---|---|
| solids content: | 35% by weight |
| sodium chloride content: | 5.5% by weight |
| coconut fatty acids aminoamide content: | ca. 0.1% by weight |
| sodium monochloroacetate: | <10 ppm |
| sodium dichloroacetate: | <10 ppm |

2.5 The method of Example 2.3. is repeated. However, the reaction mixture is heated to 180° C. in the stirred autoclave, the pressure increasing to about 8 bar. After only 1 hour, the sodium dichloroacetate is determined to be less than 10 ppm. The reaction is stopped after 4 hours. Decomposition products are detected in the product by $^1$H-NMR spectroscopy in an amount of about 5% by weight of the betaine content. The product is characterized by the following data:

| | |
|---|---|
| solids content: | 35% by weight |
| sodium chloride content: | 5.5% by weight |
| coconut fatty acids aminoamide content: | ca. 0.1% by weight |
| sodium monochloroacetate: | <10 ppm |
| sodium dichloroacetate: | <10 ppm |

2.6. Coconut fatty acids aminoamide (360 g) is added to a solution of 122.2 g (1.05 moles) of sodium monochloroacetate in 828 g of water. The reaction mixture is heated to 98° C. The pH is maintained at 8.5 to 9 by the continuous addition of 40% of sodium hydroxide solution. Samples are taken at regular intervals and investigated by thin-layer chromatography. When coconut fatty acids aminoamides can no longer be detected, the reaction temperature is increased to 140° C. and maintained there for three hours, after which the reaction is stopped. The product is characterized by the following data:

| | |
|---|---|
| solids content: | 35% by weight |
| sodium chloride content: | 5.5% by weight |
| coconut fatty acids aminoamide content: | ca. 0.1% by weight |
| sodium monochloroacetate: | <10 ppm |
| sodium dichloroacetate: | <10 ppm |

BRIEF DESCRIPTION OF THE DRAWINGS

In the FIGURE, the concentrations of sodium dichloroacetate in betaine after the reaction at 100° C. of Example 1.2., at 110° C. of Example 1.3., at 120° C. of Example 2.1., at 140° C. of Example 2.2., and at 140° C. of Example 2.3. are shown. It can be inferred from this diagram that the lower temperature of the temperature range that must be maintained for the inventive method is about 115° C. Below this temperature, there is no rapid decrease in the sodium dichloroacetate content to below 10 ppm. At the same time, the reaction time is about 2 to 8 hours, depending on the reaction temperature selected. In view of the decomposition products of Example 2.5., it can be assumed that a temperature of 180° is the upper limit for the temperature range of the inventive method; however, an upper limit of 160° C. is preferred for the reaction temperature.

What is claimed is:

1. A method for the synthesis of betaines of the general formula

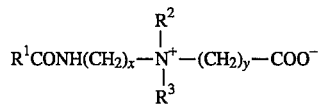

wherein
 R$^1$CO is an acyl group derived from a fatty acid or a fatty acid mixture with 6 to 8 carbon atoms,
 R$^2$ and R$^3$ are the same or different and represent alkyl groups with 1 to 4 carbon atoms,
 x=2 or 3 and
 y=1, 2 or 3,
by quaternizing the fatty acid amide dialkylamine of the general formula

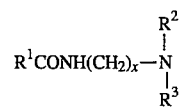

with chlorocarboxylic acids of the formula Cl(CH$_2$)$_y$COOH or their salts in aqueous solution, comprising carrying out the reaction between about 115° to 180° C., until organically bound chlorine is about ≦10 ppm, the fatty acid amide dialkylamine optionally being quaternized at least partially in a first step between about 80° to 100° C.

2. The method of claim 1, comprising that the reaction is carried out at a temperature of between about 120° to 140° C.

3. The method of claim 1, wherein the reaction is carried out until the derivatives of dichloroacetic acid can no longer be detected.

* * * * *